US006326171B1

(12) United States Patent
Selby et al.

(10) Patent No.: US 6,326,171 B1
(45) Date of Patent: *Dec. 4, 2001

(54) HEPATITIS C E1 AND E2 TRUNCATED POLYPEPTIDES AND METHODS OF OBTAINING THE SAME

(75) Inventors: Mark Selby, San Francisco; Michael Houghton, Danville, both of CA (US)

(73) Assignee: Chiron Corporation, Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/415,582

(22) Filed: Oct. 8, 1999

Related U.S. Application Data

(63) Continuation of application No. 08/506,608, filed on Jul. 25, 1995, now abandoned, which is a continuation-in-part of application No. 08/282,959, filed on Jul. 29, 1994, now abandoned.

(51) Int. Cl.[7] .............................. C12N 15/09; C12N 7/00; C12Q 1/70; A61K 39/29; A61K 39/00
(52) U.S. Cl. ..................... 435/69.3; 435/5; 435/235.1; 424/228.1; 424/185.1; 424/204.1; 530/395; 530/826
(58) Field of Search ...................... 435/5, 69.3, 235.1; 424/228.1, 189.1, 204.1; 530/395, 826

(56) References Cited

U.S. PATENT DOCUMENTS 5,942,234 * 8/1999 Ralston et al. ................... 424/228.1

FOREIGN PATENT DOCUMENTS

| WO 89/04669 | 6/1989 | (WO) . |
| WO 90/11089 | 10/1990 | (WO) . |
| WO 90/14436 | 11/1990 | (WO) . |
| WO 92/02628 | 2/1992 | (WO) . |
| WO 92/08734 | 5/1992 | (WO) . |
| WO 96/04385 | 2/1996 | (WO) . |

OTHER PUBLICATIONS

Choo et al., "Isolation of a cDNA Clone Derived from a Blood–Borne Non–A, Non–B Viral Hepatitis Genome", *Science* 244:359–362 (1989).

Choo et al., "Genetic Organization and Diversity of the Hepatitis C Virus", *Proc. Natl. Acad. Sci. USA* 88:2451–2455 (1991).

Choo et al., "Vaccination of Chimpanzees Against infection by the Hepatitis C Virus", *Proc. Natl. Acad. Sci. USA* 91:1294–1298 (1994).

Gething and Sambrook, "Construction of Influenza Haemagglutinin Genes that Code for Intracellular and Secreted Forms of the Protein", *Nature* 300:598–603 (1982).

Grakoui et al., "Expression and Identification of Hepatitis C Virus Polyprotein Cleavage Products", *J. Virol.* 67:1385–1395 (1993).

Han et al., "Characterization of the Terminal Regions of Hepatitis C Viral RNA: Identification of Conserved Sequences in the 5' Untranslated Region and Poly(A) Tails at the 3' End", *Proc. Natl. Acad. Sci. USA* 88:1711–1715 (1991).

Houghton et al., "Molecular Biology of the Hepatitis C Viruses: Implications for Diagnosis, Development and Control of Viral Disease", *Hepatology* 14:381–388 (1991).

(List continued on next page.)

Primary Examiner—Hankyel T. Park
Assistant Examiner—Stacey S Brown
(74) Attorney, Agent, or Firm—Roberta L. Robins; Alisa A. Harbin; Robert P. Blackburn

(57) ABSTRACT

Novel Hepatitis C E1 and E2 truncated polypeptides and complexes comprising these polypeptides, are disclosed. The polypeptides are C-terminally truncated to remove all or a portion of their membrane spanning domains. Hence, the polypeptides are capable of secretion when expressed recombinantly.

4 Claims, 9 Drawing Sheets

= presumptive signal sequence for E1, derived from the C-terminus of the core coding region = region of the HCV polyprotein which contributes to E1 retention within cells

OTHER PUBLICATIONS

Lanford et al., "Analysis of Hepatitis C Virus Capsid, E1, and E2/NS1 Proteins Expressed in Insect Cells", *Virology* 197:225–235 (1993).

Matsuura et al., "Processing of E1 and E2 Glycoproteins of Hepatitis C Virus Expressed in Mammalian and Insect Cells," *Virology* 205:(1):141–150 (1994).

Mizushima et al., "Analysis of N–Terminal Processing of Hepatitis C Virus Nonstructural Protein 2," *Journal of Virology* 68(4):2731–2734 (1994).

Nishihara et al., "Secretion and Purification of Hepatitis C Virus NS1 . . . ," *Gene* 129:207–214 (1993).

Ralston et al., "Characterization of Hepatitis C Virus Envelope Glycoprotein Complexes Expressed by Recombinant Vaccinia Viruses", *J. Virol.* 67:6753–6761 (1993).

Rose and Bergmann, "Expression from Cloned cDNA of Cell–Surface Secreted Forms of the Glycoprotein of Vesicular Stomatitis Virus in Eucaryotic Cells", *Cell* 30:753–762 (1982).

Selby et al., "Expression, Identification and Subcellular Localization of the Proteins Encoded by the Hepatitis C Viral Genome," *J. Gen. Virol.* 74(6):1103–1113 (1993).

Selby et al., "Complex Processing and Protein: Protein Interactions in the E2:NS2 Region of HCV," *Virology* 204(1):114–122 (1994).

Simmonds et al., "Classification of Hepatitis C Virus Into Six Major Genotypes and a Series of Subtypes by Phylogenetic Analysis of the NS–5 Region", *J. Gen. Virol.* 74:2391–2399 (1993).

Spaete et al., "Characterization of the Hepatitis C Virus E2/NS1 Gene Product Expressed in Mammalian Cells", *Virology* 188:819–830 (1992).

Sveda, et al., "Cell Surface Expression of the Influenza Virus Hemagglutinin Requires the Hydrophobic Carboxy–Terminal Sequences", *Cell* 30:649–656 (1982).

Tomei et al., "NS3 Is a Serine Protease Required for Processing of Hepatitis C Virus Polyprotein", *Virol.* 67:4017–4026 (1993).

\* cited by examiner

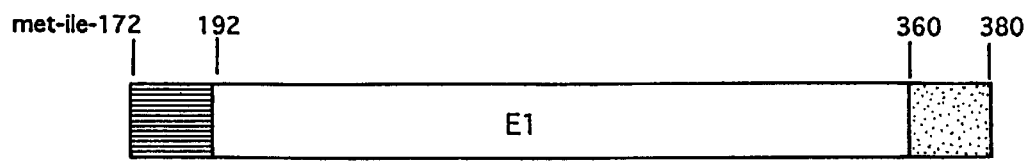
 = presumptive signal sequence for E1, derived from the C-terminus of the core coding region
 = region of the HCV polyprotein which contributes to E1 retention within cells
FIG. 1

```
170   MetIleCysSerPheSerIlePheLeuLeuAlaLeuLeuSerCysLeuThrValProAla
      ATGATTTGCTCTTTCTCTATCTTCCTTCTGGCCCTGCTCTCTTGCTTGACTGTGCCCGCT
      TACTAAACGAGAAAGAGATAGAAGGAAGACCGGGACGAGAGAACGAACTGACACGGGCGA

Mature E1
190   SerAlaTyrGlnValArgAsnSerThrGlyLeuTyrHisValThrAsnAspCysProAsn
      TCGGCCTACCAAGTGCGCAACTCCACGGGGCTCTACCACGTCACCAATGATTGCCCTAAC
      AGCCGGATGGTTCACGCGTTGAGGTGCCCCGAGATGGTGCAGTGGTTACTAACGGGATTG 210   SerSerIleValTyrGluAlaAlaAspAlaIleLeuHisThrProGlyCysValProCys
      TCGAGTATTGTGTACGAGGCGGCCGATGCCATCCTGCACACTCCGGGGTGCGTCCCTTGC
      AGCTCATAACACATGCTCCGCCGGCTACGGTAGGACGTGTGAGGCCCCACGCAGGGAACG 230   ValArgGluGlyAsnAlaSerArgCysTrpValAlaMetThrProThrValAlaThrArg
      GTTCGTGAGGGCAACGCCTCGAGGTGTTGGGTGGCGATGACCCCTACGGTGGCCACCAGG
      CAAGCACTCCCGTTGCGGAGCTCCACAACCCACCGCTACTGGGGATGCCACCGGTGGTCC 250   AspGlyLysLeuProAlaThrGlnLeuArgArgHisIleAspLeuLeuValGlySerAla
      GATGGCAAACTCCCCGCGACGCAGCTTCGACGTCACATCGATCTGCTTGTCGGGAGCGCC
      CTACCGTTTGAGGGGCGCTGCGTCGAAGCTGCAGTGTAGCTAGACGAACAGCCCTCGCGG 270   ThrLeuCysSerAlaLeuTyrValGlyAspLeuCysGlySerValPheLeuValGlyGln
      ACCCTCTGTTCGGCCCTCTACGTGGGGGACCTCTGCGGGTCTGTCTTTCTTGTCGGCCAA
      TGGGAGACAAGCCGGGAGATGCACCCCCTGGAGACGCCCAGACAGAAAGAACAGCCGGTT 290   LeuPheThrPheSerProArgArgHisTrpThrThrGlnGlyCysAsnCysSerIleTyr
      CTGTTTACCTTCTCTCCCAGGCGCCACTGGACGACGCAAGGTTGCAATTGCTCTATCTAT
      GACAAATGGAAGAGAGGGTCCGCGGTGACCTGCTGCGTTCCAACGTTAACGAGATAGATA 310   ProGlyHisIleThrGlyHisArgMetAlaTrpAspMetMetMetAsnTrpSerProThr
      CCCGGCCATATAACGGGTCACCGCATGGCATGGGATATGATGATGAACTGGTCCCCTACG
      GGGCCGGTATATTGCCCAGTGGCGTACCGTACCCTATACTACTACTTGACCAGGGGATGC 330   ThrAlaLeuValMetAlaGlnLeuLeuArgIleProGlnAlaIleLeuAspMetIleAla
      ACGGCGTTGGTAATGGCTCAGCTGCTCCGGATCCCACAAGCCATCTTGGACATGATCGCT
      TGCCGCAACCATTACCGAGTCGACGAGGCCTAGGGTGTTCGGTAGAACCTGTACTAGCGA C-terminal Anchor
350   GlyAlaHisTrpGlyValLeuAlaGlyIleAlaTyrPheSerMetValGlyAsnTrpAla
      GGTGCTCACTGGGGAGTCCTGGCGGGCATAGCGTATTTCTCCATGGTGGGGAACTGGGCG
      CCACGAGTGACCCCTCAGGACCGCCCGTATCGCATAAAGAGGTACCACCCCTTGACCCGC 370   LysValLeuValValLeuLeuLeuPheAlaGlyOP
      AAGGTCCTGGTAGTGCTGCTGCTATTTGCCGGCTGA
      TTCCAGGACCATCACGACGACGATAAACGGCCGACT
```

FIG. 2

```
364  MetValGlyAsnTrpAlaLysValLeuValValLeuLeuLeuPheAlaGlyValAspAla
     ATGGTGGGGAACTGGGCGAAGGTCCTGGTAGTGCTGCTGCTATTTGCCGGCGTCGACGCG
     TACCACCCCTTGACCCGCTTCCAGGACCATCACGACGACGATAAACGGCCGCAGCTGCGC

Mature E2
384  GluThrHisValThrGlyGlySerAlaGlyHisThrValSerGlyPheValSerLeuLeu
     GAAACCCACGTCACCGGGGGAAGTGCCGGCCACACTGTGTCTGGATTTGTTAGCCTCCTC
     CTTTGGGTGCAGTGGCCCCCTTCACGGCCGGTGTGACACAGACCTAAACAATCGGAGGAG 404  AlaProGlyAlaLysGlnAsnValGlnLeuIleAsnThrAsnGlySerTrpHisLeuAsn
     GCACCAGGCGCCAAGCAGAACGTCCAGCTGATCAACACCAACGGCAGTTGGCACCTCAAT
     CGTGGTCCGCGGTTCGTCTTGCAGGTCGACTAGTTGTGGTTGCCGTCAACCGTGGAGTTA 424  SerThrAlaLeuAsnCysAsnAspSerLeuAsnThrGlyTrpLeuAlaGlyLeuPheTyr
     AGCACGGCCCTGAACTGCAATGATAGCCTCAACACCGGCTGGTTGGCAGGGCTTTTCTAT
     TCGTGCCGGGACTTGACGTTACTATCGGAGTTGTGGCCGACCAACCGTCCCGAAAAGATA 444  HisHisLysPheAsnSerSerGlyCysProGluArgLeuAlaSerCysArgProLeuThr
     CACCACAAGTTCAACTCTTCAGGCTGTCCTGAGAGGCTAGCCAGCTGCCGACCCCTTACC
     GTGGTGTTCAAGTTGAGAAGTCCGACAGGACTCTCCGATCGGTCGACGGCTGGGGAATGG 464  AspPheAspGlnGlyTrpGlyProIleSerTyrAlaAsnGlySerGlyProAspGlnArg
     GATTTTGACCAGGGCTGGGGCCCTATCAGTTATGCCAACGGAAGCGGCCCCGACCAGCGC
     CTAAAACTGGTCCCGACCCCGGGATAGTCAATACGGTTGCCTTCGCCGGGGCTGGTCGCG 484  ProTyrCysTrpHisTyrProProLysProCysGlyIleValProAlaLysSerValCys
     CCCTACTGCTGGCACTACCCCCCAAAACCTTGCGGTATTGTGCCCGCGAAGAGTGTGTGT
     GGGATGACGACCGTGATGGGGGGTTTTGGAACGCCATAACACGGGCGCTTCTCACACACA 504  GlyProValTyrCysPheThrProSerProValValValGlyThrThrAspArgSerGly
     GGTCCGGTATATTGCTTCACTCCCAGCCCCGTGGTGGTGGGAACGACCGACAGGTCGGGC
     CCAGGCCATATAACGAAGTGAGGGTCGGGGCACCACCACCCTTGCTGGCTGTCCAGCCCG 524  AlaProThrTyrSerTrpGlyGluAsnAspThrAspValPheValLeuAsnAsnThrArg
     GCGCCCACCTACAGCTGGGGTGAAAATGATACGGACGTCTTCGTCCTTAACAATACCAGG
     CGCGGGTGGATGTCGACCCCACTTTTACTATGCCTGCAGAAGCAGGAATTGTTATGGTCC 544  ProProLeuGlyAsnTrpPheGlyCysThrTrpMetAsnSerThrGlyPheThrLysVal
     CCACCGCTGGGCAATTGGTTCGGTTGTACCTGGATGAACTCAACTGGATTCACCAAAGTG
     GGTGGCGACCCGTTAACCAAGCCAACATGGACCTACTTGAGTTGACCTAAGTGGTTTCAC 564  CysGlyAlaProProCysValIleGlyGlyAlaGlyAsnAsnThrLeuHisCysProThr
     TGCGGAGCGCCTCCTTGTGTCATCGGAGGGGCGGGCAACAACACCCTGCACTGCCCCACT
     ACGCCTCGCGGAGGAACACAGTAGCCTCCCCGCCCGTTGTTGTGGGACGTGACGGGGTGA 584  AspCysPheArgLysHisProAspAlaThrTyrSerArgCysGlySerGlyProTrpIle
     GATTGCTTCCGCAAGCATCCGGACGCCACATACTCTCGGTGCGGCTCCGGTCCCTGGATC
     CTAACGAAGGCGTTCGTAGGCCTGCGGTGTATGAGAGCCACGCCGAGGCCAGGGACCTAG 604  ThrProArgCysLeuValAspTyrProTyrArgLeuTrpHisTyrProCysThrIleAsn
     ACACCCAGGTGCCTGGTCGACTACCCGTATAGGCTTTGGCATTATCCTTGTACCATCAAC
     TGTGGGTCCACGGACCAGCTGATGGGCATATCCGAAACCGTAATAGGAACATGGTAGTTG 624  TyrThrIlePheLysIleArgMetTyrValGlyGlyValGluHisArgLeuGluAlaAla
     TACACCATATTTAAAATCAGGATGTACGTGGGAGGGGTCGAACACAGGCTGGAAGCTGCC
     ATGTGGTATAAATTTTAGTCCTACATGCACCCTCCCCAGCTTGTGTCCGACCTTCGACGG 644  CysAsnTrpThrArgGlyGluArgCysAspLeuGluAspArgAspArgSerGluLeuSer
     TGCAACTGGACGCGGGGCGAACGTTGCGATCTGGAAGATAGGGACAGGTCCGAGCTCAGC
     ACGTTGACCTGCGCCCCGCTTGCAACGCTAGACCTTCTATCCCTGTCCAGGCTCGAGTCG
```

FIG. 4A

```
664  ProLeuLeuLeuThrThrThrGlnTrpGlnValLeuProCysSerPheThrThrLeuPro
     CCGTTACTGCTGACCACTACACAGTGGCAGGTCCTCCCGTGTTCCTTCACAACCCTGCCA
     GGCAATGACGACTGGTGATGTGTCACCGTCCAGGAGGGCACAAGGAAGTGTTGGGACGGT

684  AlaLeuSerThrGlyLeuIleHisLeuHisGlnAsnIleValAspValGlnTyrLeuTyr
     GCCTTGTCCACCGGCCTCATCCACCTCCACCAGAACATTGTGGACGTGCAGTACTTGTAC
     CGGAACAGGTGGCCGGAGTAGGTGGAGGTGGTCTTGTAACACCTGCACGTCATGAACATG

704  GlyValGlySerSerIleAlaSerTrpAlaIleLysTrpGluTyrValValLeuLeuPhe
     GGGGTGGGGTCAAGCATCGCGTCCTGGGCCATTAAGTGGGAGTACGTCGTCCTCCTGTTC
     CCCCACCCCAGTTCGTAGCGCAGGACCCGGTAATTCACCCTCATGCAGCAGGAGGACAAG

C-terminal anchor
724  LeuLeuLeuAlaAspAlaArgValCysSerCysLeuTrpMetMetLeuLeuIleSerGln
     CTTCTGCTTGCAGACGCGCGCGTCTGCTCCTGCTTGTGGATGATGCTACTCATATCCCAA
     GAAGACGAACGTCTGCGCGCGCAGACGAGGACGAACACCTACTACGATGAGTATAGGGTT NS2A
744  AlaGluAlaAlaLeuGluAsnLeuValIleLeuAsnAlaAlaSerLeuAlaGlyThrHis
     GCGGAAGCGGCTTTGGAGAACCTCGTAATACTTAATGCAGCATCCCTGGCCGGGACGCAC
     CGCCTTCGCCGAAACCTCTTGGAGCATTATGAATTACGTCGTAGGGACCGGCCCTGCGTG 764  GlyLeuValSerPheLeuValPhePheCysPheAlaTrpTyrLeuLysGlyLysTrpVal
     GGTCTTGTATCCTTCCTCGTGTTCTTCTGCTTTGCATGGTATCTGAAGGGTAAGTGGGTG
     CCAGAACATAGGAAGGAGCACAAGAAGACGAAACGTACCATAGACTTCCCATTCACCCAC 784  ProGlyAlaValTyrThrPheTyrGlyMetTrpProLeuLeuLeuLeuLeuAlaLeu
     CCCGGAGCGGTCTACACCTTCTACGGGATGTGGCCTCTCCTCCTGCTCCTGTTGGCGTTG
     GGGCCTCGCCAGATGTGGAAGATGCCCTACACCGGAGAGGAGGACGAGGACAACCGCAAC NS2B
804  ProGlnArgAlaTyrAlaLeuAspThrGluValAlaAlaSerCysGlyGlyValValLeu
     CCCCAGCGGGCGTACGCGCTGGACACGGAGGTGGCCGCGTCGTGTGGCGGTGTTGTTCTC
     GGGGTCGCCCGCATGCGCGACCTGTGCCTCCACCGGCGCAGCACACCGCCACAACAAGAG 824  ValGlyLeuMetAlaLeuThrLeuSerProTyrTyrLysArgTyrIleSerTrpCysLeu
     GTCGGGTTGATGGCGCTAACTCTGTCACCATATTACAAGCGCTATATCAGCTGGTGCTTG
     CAGCCCAACTACCGCGATTGAGACAGTGGTATAATGTTCGCGATATAGTCGACCACGAAC 844  TrpTrpLeuGlnTyrPheLeuThrArgValGluAlaGlnLeuHisValTrpIleProPro
     TGGTGGCTTCAGTATTTTCTGACCAGAGTGGAAGCGCAACTGCACGTGTGGATTCCCCCC
     ACCACCGAAGTCATAAAAGACTGGTCTCACCTTCGCGTTGACGTGCACACCTAAGGGGGG 864  LeuAsnValArgGlyGlyArgAspAlaValIleLeuLeuMetCysAlaValHisProThr
     CTCAACGTCCGAGGGGGGCGCGACGCCGTCATCTTACTCATGTGTGCTGTACACCCGACT
     GAGTTGCAGGCTCCCCCCGCGCTGCGGCAGTAGAATGAGTACACACGACATGTGGGCTGA 884  LeuValPheAspIleThrLysLeuLeuLeuAlaValPheGlyProLeuTrpIleLeuGln
     CTGGTATTTGACATCACCAAATTGCTGCTGGCCGTCTTCGGACCCCTTTGGATTCTTCAA
     GACCATAAACTGTAGTGGTTTAACGACGACCGGCAGAAGCCTGGGGAAACCTAAGAAGTT 904  AlaSerLeuLeuLysValProTyrPheValArgValGlnGlyLeuLeuArgPheCysAla
     GCCAGTTTGCTTAAAGTACCCTACTTTGTGCGCGTCCAAGGCCTTCTCCGGTTCTGCGCG
     CGGTCAAACGAATTTCATGGGATGAAACACGCGCAGGTTCCGGAAGAGGCCAAGACGCGC 924  LeuAlaArgLysMetIleGlyGlyHisTyrValGlnMetValIleIleLysLeuGlyAla
     TTAGCGCGGAAGATGATCGGAGGCCATTACGTGCAAATGGTCATCATTAAGTTAGGGGCG
     AATCGCGCCTTCTACTAGCCTCCGGTAATGCACGTTTACCAGTAGTAATTCAATCCCCGC 944  LeuThrGlyThrTyrValTyrAsnHisLeuThrProLeuArgAspTrpAlaHisAsnGly
     CTTACTGGCACCTATGTTTATAACCATCTCACTCCTCTTCGGGACTGGGCGCACAACGGC
     GAATGACCGTGGATACAAATATTGGTAGAGTGAGGAGAAGCCCTGACCCGCGTGTTGCCG
```

FIG. 4B

```
 964   LeuArgAspLeuAlaValAlaValGluProValValPheSerGlnMetGluThrLysLeu
       TTGCGAGATCTGGCCGTGGCTGTAGAGCCAGTCGTCTTCTCCCAAATGGAGACCAAGCTC
       AACGCTCTAGACCGGCACCGACATCTCGGTCAGCAGAAGAGGGTTTACCTCTGGTTCGAG

984   IleThrTrpGlyAlaAspThrAlaAlaCysGlyAspIleIleAsnGlyLeuProValSer
       ATCACGTGGGGGGCAGATACCGCCGCGTGCGGTGACATCATCAACGGCTTGCCTGTTTCC
       TAGTGCACCCCCCGTCTATGGCGGCGCACGCCACTGTAGTAGTTGCCGAACGGACAAAGG

1004   AlaArgArgGlyArgGluIleLeuLeuGlyProAlaAspGlyMetValSerLysGlyTrp
       GCCCGCAGGGGCCGGGAGATACTGCTCGGGCCAGCCGATGGAATGGTCTCCAAGGGTTGG
       CGGGCGTCCCCGGCCCTCTATGACGAGCCCGGTCGGCTACCTTACCAGAGGTTCCCAACC

1024   ArgLeuLeu
       AGGTTGCTG
       TCCAACGAC
```

FIG. 4C

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 211 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 1:

Met Ile Cys Ser Phe Ser Ile Phe Leu Leu Ala Leu Leu Ser Cys Leu
1               5                   10                  15

Thr Val Pro Ala Ser Ala Tyr Gln Val Arg Asn Ser Thr Gly Leu Tyr
            20                  25                  30

His Val Thr Asn Asp Cys Pro Asn Ser Ser Ile Val Tyr Glu Ala Ala
        35                  40                  45

Asp Ala Ile Leu His Thr Pro Gly Cys Val Pro Cys Val Arg Glu Gly
    50                  55                  60

```
Asn Ala Ser Arg Cys Trp Val Ala Met Thr Pro Thr Val Ala Thr Arg
 65                  70                  75                  80

Asp Gly Lys Leu Pro Ala Thr Gln Leu Arg Arg His Ile Asp Leu Leu
                 85                  90                  95

Val Gly Ser Ala Thr Leu Cys Ser Ala Leu Tyr Val Gly Asp Leu Cys
            100                 105                 110

Gly Ser Val Phe Leu Val Gly Gln Leu Phe Thr Phe Ser Pro Arg Arg
            115                 120                 125

His Trp Thr Thr Gln Gly Cys Asn Cys Ser Ile Tyr Pro Gly His Ile
130                 135                 140

Thr Gly His Arg Met Ala Trp Asp Met Met Met Asn Trp Ser Pro Thr
145                 150                 155                 160

Thr Ala Leu Val Met Ala Gln Leu Leu Arg Ile Pro Gln Ala Ile Leu
            165                 170                 175

Asp Met Ile Ala Gly Ala His Trp Gly Val Leu Ala Gly Ile Ala Tyr
            180                 185                 190

Phe Ser Met Val Gly Asn Trp Ala Lys Val Leu Val Val Leu Leu Leu
            195                 200                 205

Phe Ala Gly
210
```

(2) INFORMATION FOR SEQ ID NO: 2:

(i) SEQUENCE CHARACTERISTICS:
        (A) LENGTH: 636 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

```
ATGATTTGCT CTTTCTCTAT CTTCCTTCTG GCCCTGCTCT CTTGCTTGAC TGTGCCCGCT     60
TCGGCCTACC AAGTGCGCAA CTCCACGGGG CTCTACCACG TCACCAATGA TTGCCCTAAC    120
TCGAGTATTG TGTACGAGGC GGCCGATGCC ATCCTGCACA CTCCGGGGTG CGTCCCTTGC    180
GTTCGCGAGG GCAACGCCTC GAGGTGTTGG GTGGCGATGA CCCCTACGGT GGCCACCAGG    240
GATGGCAAAC TCCCCGCGAC GCAGCTTCGA CGTCACATCG ATCTGCTTGT CGGGAGCGCC    300
ACCCTCTGTT CGGCCCTCTA CGTGGGGGAC CTGTGCGGGT CTGTCTTTCT TGTCGGCCAA    360
CTGTTTACCT TCTCTCCCAG GCGCCACTGG ACGACGCAAG GTTGCAATTG CTCTATCTAT    420
CCCGGCCATA TAACGGGTCA CCGCATGGCA TGGGATATGA TGATGAACTG GTCCCCTACG    480
ACGGCGTTGG TAATGGCTCA GCTGCTCCGG ATCCCACAAG CCATCTTGGA CATGATCGCT    540
GGTGCTCACT GGGGAGTCCT GGCGGGCATA GCGTATTTCT CCATGGTGGG GAACTGGGCG    600
AAGGTCCTGG TAGTGCTGCT GCTATTTGCC GGCTGA                              636
```

(2) INFORMATION FOR SEQ ID NO: 3:

(i) SEQUENCE CHARACTERISTICS:
        (A) LENGTH: 663 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

-continued

```
Met Val Gly Asn Trp Ala Lys Val Leu Val Leu Leu Leu Phe Ala
1               5                   10                  15

Gly Val Asp Ala Glu Thr His Val Thr Gly Ser Ala Gly His Thr
                20                  25              30

Val Ser Gly Phe Val Ser Leu Leu Ala Pro Gly Ala Lys Gln Asn Val
            35              40              45

Gln Leu Ile Asn Thr Asn Gly Ser Trp His Leu Asn Ser Thr Ala Leu
    50                  55                  60

Asn Cys Asn Asp Ser Leu Asn Thr Gly Trp Leu Ala Gly Leu Phe Tyr
65                  70                  75                  80

His His Lys Phe Asn Ser Ser Gly Cys Pro Glu Arg Leu Ala Ser Cys
                85                  90                  95

Arg Pro Leu Thr Asp Phe Asp Gln Gly Trp Gly Pro Ile Ser Tyr Ala
                100                 105                 110

Asn Gly Ser Gly Pro Asp Gln Arg Pro Tyr Cys Trp His Tyr Pro Pro
            115                 120                 125

Lys Pro Cys Gly Ile Val Pro Ala Lys Ser Val Cys Gly Pro Val Tyr
            130                 135                 140

Cys Phe Thr Pro Ser Pro Val Val Gly Thr Thr Asp Arg Ser Gly
145                 150                 155                 160

Ala Pro Thr Tyr Ser Trp Gly Glu Asn Asp Thr Asp Val Phe Val Leu
                165                 170                 175

Asn Asn Thr Arg Pro Pro Leu Gly Asn Trp Phe Gly Cys Thr Trp Met
            180                 185                 190

Asn Ser Thr Gly Phe Thr Lys Val Cys Gly Ala Pro Pro Cys Val Ile
            195                 200                 205

Gly Gly Ala Gly Asn Asn Thr Leu His Cys Pro Thr Asp Cys Phe Arg
    210                 215                 220

Lys His Pro Asp Ala Thr Tyr Ser Arg Cys Gly Ser Gly Pro Trp Ile
225                 230                 235                 240

Thr Pro Arg Cys Leu Val Asp Tyr Pro Tyr Arg Leu Trp His Tyr Pro
            245                 250                 255

Cys Thr Ile Asn Tyr Thr Ile Phe Lys Ile Arg Met Tyr Val Gly Gly
            260                 265                 270

Val Glu His Arg Leu Glu Ala Ala Cys Asn Trp Thr Arg Gly Glu Arg
    275                 280                 285

Cys Asp Leu Glu Asp Arg Asp Arg Ser Glu Leu Ser Pro Leu Leu Leu
    290                 295                 300

Thr Thr Thr Gln Trp Gln Val Leu Pro Cys Ser Phe Thr Thr Leu Pro
305                 310                 315                 320

Ala Leu Ser Thr Gly Leu Ile His Leu His Gln Asn Ile Val Asp Val
                325                 330                 335

Gln Tyr Leu Tyr Gly Val Gly Ser Ser Ile Ala Ser Trp Ala Ile Lys
                340                 345                 350

Trp Glu Tyr Val Val Leu Leu Phe Leu Leu Ala Asp Ala Arg Val
                355                 360                 365

Cys Ser Cys Leu Trp Met Met Leu Leu Ile Ser Gln Ala Glu Ala Ala
370                 375                 380

Leu Glu Asn Leu Val Ile Leu Asn Ala Ala Ser Leu Ala Gly Thr His
385                 390                 395                 400

Gly Leu Val Ser Phe Leu Val Phe Phe Cys Phe Ala Trp Tyr Leu Lys
            405                 410                 415

Gly Lys Trp Val Pro Gly Ala Val Tyr Thr Phe Tyr Gly Met Trp Pro
```

```
                    420              425              430
Leu Leu Leu Leu Leu Leu Ala Leu Pro Gln Arg Ala Tyr Ala Leu Asp
            435              440              445

Thr Glu Val Ala Ala Ser Cys Gly Gly Val Val Leu Val Gly Leu Met
450              455              460

Ala Leu Thr Leu Ser Pro Tyr Tyr Lys Arg Tyr Ile Ser Trp Cys Leu
465              470              475              480

Trp Trp Leu Gln Tyr Phe Leu Thr Arg Val Glu Ala Gln Leu His Val
            485              490              495

Trp Ile Pro Pro Leu Asn Val Arg Gly Gly Arg Asp Ala Val Ile Leu
            500              505              510

Leu Met Cys Ala Val His Pro Thr Leu Val Phe Asp Ile Thr Lys Leu
            515              520              525

Leu Leu Ala Val Phe Gly Pro Leu Trp Ile Leu Gln Ala Ser Leu Leu
            530              535              540

Lys Val Pro Tyr Phe Val Arg Val Gln Gly Leu Leu Arg Phe Cys Ala
545              550              555              560

Leu Ala Arg Lys Met Ile Gly Gly His Tyr Val Gln Met Val Ile Ile
            565              570              575

Lys Leu Gly Ala Leu Thr Gly Thr Tyr Val Tyr Asn His Leu Thr Pro
            580              585              590

Leu Arg Asp Trp Ala His Asn Gly Leu Arg Asp Leu Ala Val Ala Val
            595              600              605

Glu Pro Val Val Phe Ser Gln Met Glu Thr Lys Leu Ile Thr Trp Gly
            610              615              620

Ala Asp Thr Ala Ala Cys Gly Asp Ile Ile Asn Gly Leu Pro Val Ser
625              630              635              640

Ala Arg Arg Gly Arg Glu Ile Leu Leu Gly Pro Ala Asp Gly Met Val
            645              650              655

Ser Lys Gly Trp Arg Leu Leu
            660

(2) INFORMATION FOR SEQ ID NO: 4:

(i) SEQUENCE CHARACTERISTICS:
        (A) LENGTH: 1989 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

ATGGTGGGGA ACTGGGCGAA GGTCCTGGTA GTGCTGCTGC TATTTGCCGG CGTCGACGCG      60

GAAACCCACG TCACCGGGGG AAGTGCCGGC CACACTGTGT CTGGATTTGT TAGCCTCCTC     120

GCACCAGGCG CCAAGCAGAA CGTCCAGCTG ATCAACACCA ACGGCAGTTG GCACCTCAAT     180

AGCACGGCCC TGAACTGCAA TGATAGCCTC AACACCGGCT GGTTGGCAGG GCTTTTCTAT     240

CACCACAAGT TCAACTCTTC AGGCTGTCCT GAGAGGCTAG CCAGCTGCCG ACCCCTTACC     300

GATTTTGACC AGGGCTGGGG CCCTATCAGT TATGCCAACG GAAGCGGCCC CGACCAGCGC     360

CCCTACTGCT GGCACTACCC CCCAAAACCT TGCGGTATTG TGCCCGCGAA GAGTGTGTGT     420

GGTCCGGTAT ATTGCTTCAC TCCCAGCCCC GTGGTGGTGG AACGACCGA CAGGTCGGGC      480

GCGCCCACCT ACAGCTGGGG TGAAAATGAT ACGGACGTCT TCGTCCTTAA CAATACCAGG     540

CCACCGCTGG GCAATTGGTT CGGTTGTACC TGGATGAACT CAACTGGATT CACCAAAGTG     600
```

```
TGCGGAGCGC CTCCTTGTGT CATCGGAGGG GCGGGCAACA ACACCCTGCA CTGCCCCACT    660
GATTGCTTCC GCAAGCATCC GGACGCCACA TACTCTCGGT GCGGCTCCGG TCCCTGGATC    720
ACACCCAGGT GCCTGGTCGA CTACCCGTAT AGGCTTTGGC ATTATCCTTG TACCATCAAC    780
TACACTATAT TTAAAATCAG GATGTACGTG GGAGGGGTCG AGCACAGGCT GGAAGCTGCC    840
TGCAACTGGA CGCGGGGCGA ACGTTGCGAT CTGGAAGATA GGGACAGGTC CGAGCTCAGC    900
CCGTTACTGC TGACCACTAC ACAGTGGCAG GTCCTCCCGT GTTCCTTCAC AACCCTGCCA    960
GCCTTGTCCA CCGGCCTCAT CCACCTCCAC CAGAACATTG TGGACGTGCA GTACTTGTAC   1020
GGGGTGGGGT CAAGCATCGC GTCCTGGGCC ATTAAGTGGG AGTACGTCGT CCTCCTGTTC   1080
CTTCTGCTTG CAGACGCGCG CGTCTGCTCC TGCTTGTGGA TGATGCTACT CATATCCCAA   1140
GCGGAAGCGG CTTTGGAGAA CCTCGTAATA CTTAATGCAG CATCCCTGGC CGGGACGCAC   1200
GGTCTTGTAT CCTTCCTCGT GTTCTTCTGC TTTGCATGGT ATCTGAAGGG TAAGTGGGTG   1260
CCCGGAGCGG TCTACACCTT CTACGGGATG TGGCCTCTCC TCCTGCTCCT GTTGGCGTTG   1320
CCCCAGCGGG CGTACGCGCT GGACACGGAG GTGGCCGCGT CGTGTGGCGG TGTTGTTCTC   1380
GTCGGGTTGA TGGCGCTAAC TCTGTCACCA TATTACAAGC GCTATATCAG CTGGTGCTTG   1440
TGGTGGCTTC AGTATTTTCT GACCAGAGTG GAAGCGCAAC TGCACGTGTG GATTCCCCCC   1500
CTCAACGTCC GAGGGGGGCG CGACGCCGTC ATCTTACTCA TGTGTGCTGT ACACCCGACT   1560
CTGGTATTTG ACATCACCAA ATTGCTGCTG GCCGTCTTCG GACCCCTTTG GATTCTTCAA   1620
GCCAGTTTGC TTAAAGTACC CTACTTTGTG CGCGTCCAAG GCCTTCTCCG GTTCTGCGCG   1680
TTAGCGCGGA AGATGATCGG AGGCCATTAC GTGCAAATGG TCATCATTAA GTTAGGGGCG   1740
CTTACTGGCA CCTATGTTTA TAACCATCTC ACTCCTCTTC GGGACTGGGC GCACAACGGC   1800
TTGCGAGATC TGGCCGTGGC TGTAGAGCCA GTCGTCTTCT CCCAAATGGA GACCAAGCTC   1860
ATCACGTGGG GGGCAGATAC CGCCGCGTGC GGTGACATCA TCAACGGCTT GCCTGTTTCC   1920
GCCCGCAGGG GCCGGGAGAT ACTGCTCGGG CCAGCCGATG GAATGGTCTC CAAGGGTTGG   1980
AGGTTGCTG                                                          1989
```

HEPATITIS C E1 AND E2 TRUNCATED POLYPEPTIDES AND METHODS OF OBTAINING THE SAME

CROSS-REFERENCE TO RELATED APPLICATION

This application is a continuation of U.S. patent application Ser. No. 08/506,608, filed Jul. 25, 1995, now abandoned, which is a continuation-in-part of U.S. patent application Ser. No. 08/282,959, filed Jul. 29, 1994, now abandoned, from which applications priority is claimed pursuant to 35 U.S.C. §120 and which applications are incorporated herein by reference in their entireties.

BACKGROUND OF THE INVENTION

1. Technical Field

The present invention pertains generally to viral proteins. In particular, the invention relates to truncated, secreted forms of hepatitis C virus E1 and E2 proteins and the isolation and recombinant production of the same.

2. Background of the Invention

Hepatitis C Virus (HCV) is the principal cause of parenteral non-A, non-B hepatitis which is transmitted largely through blood transfusion and sexual contact. The virus is present in between 0.4 to 2.0% of blood donors. Chronic hepatitis develops in approximately 50% of infections and of these, approximately 20% of infected individuals develop liver cirrhosis which sometimes leads to hepatocellular carcinoma. Accordingly, the study and control of the disease is of medical importance.

The viral genomic sequence of HCV is known, as are methods for obtaining the sequence. See, e.g., International Publication Nos. WO 89/04669; WO 90/11089; and WO 90/14436. In particular, HCV has a 9.5 kb positive-sense, single-stranded RNA genome and is a member of the Flaviridae family of viruses. Currently, there are 6 distinct, but related genotypes of HCV based on phylogenetic analyses (Simmonds et al., *J. Gen. Virol.* (1993) 74:2391–2399). The virus encodes a single polyprotein having more than 3000 amino acid residues (Choo et al., *Science* (1989) 244:359–362; Choo et al., *Proc. Natl. Acad. Sci. USA* (1991) 88:2451–2455; Han et al., *Proc. Natl. Acad. Sci. USA* (1991) 88:1711–1715). The polyprotein is processed co- and post-translationally into both structural and non-structural (NS) proteins.

In particular, there are three putative structural proteins, consisting of the N-terminal nucleocapsid protein (termed "core") and two envelope glycoproteins, "E1" (also known as E) and "E2" (also known as E2/NS1). (See, Houghton et al., *Hepatology* (1991) 14:381–388, for a discussion of HCV proteins, including E1 and E2.) E1 is detected as a 32–35 kDa species and is converted into a single endo H-sensitive band of approximately 18 kDa. By contrast, E2 displays a complex pattern upon immunoprecipitation consistent with the generation of multiple species (Grakoui et al., *J. Virol.* (1993) 67:1385–1395; Tomei et al., *J. Virol.* (1993) 67:4017–4026.). The HCV envelope glycoproteins E1 and E2 form a stable complex that is co-immunoprecipitable (Grakoui et al., *J. Virol.* (1993) 67:1385–1395; Lanford et al., *Virology* (1993) 197:225–235; Ralston et al., *J. Virol.* (1993) 67:6753–6761). The HCV E1 and E2 glycoproteins are of considerable interest because they have been shown to be protective in primate studies. (Choo et al., *Proc. Natl. Acad. Sci. USA* (1994) 91:1294–1298).

The envelope of the HCV virion remains uncharacterized. Thus, expression studies using recombinant cDNA templates are the only means currently available to study envelope biosynthesis. E1 and E2 are retained within cells and lack complex carbohydrate when expressed stably or in a transient Vaccinia virus system (Spaete et al., *Virology* (1992) 188:819–830; Ralston et al., *J. Virol.* (1993) 67:6753–6761). Since the E1 and E2 proteins are normally membrane-bound in these expression systems, it would be desirable to produce secreted forms to facilitate purification of the proteins for further use.

It has been found that removal of the transmembrane domain of the viral cell surface glycoproteins of influenza virus (Sveda, et al., *Cell* (1982) 30:649–656; Gething and Sambrook, *Nature* (1982) 300:598–603) and vesicular stomatitis virus (Rose and Bergmann, *Cell* (1982) 30:753–762) results in secretion of the truncated glycoprotein from mammalian host cells. See also EPO Publication No. 139,417. Similarly, truncated cytomegalovirus gH is secreted when expressed in baculovirus cells (International Publication No. WO 92/02628, published 20 February 1992). A C-terminally truncated HCV E2 molecule, capable of secretion from mammalian cells, has been described. Spaete et al., *Virology* (1992) 188:819–830 However, the transmembrane anchor region of E1 has not heretofore been elucidated and hence the production of truncated forms of HCV E1 for secretion has not been previously disclosed. Furthermore, complexes of truncated, secreted E1 and E2 polypeptides have not been previously described.

SUMMARY OF THE INVENTION

The present invention is based on the elucidation of sequences of E1 and E2 important for anchoring the proteins to the endoplasmic reticulum (ER) and for co-precipitation of E2 with E1. Thus, the elimination of these sequences serves to produce truncated forms of the glycoproteins which are secreted rather than retained in the ER membrane. Furthermore, truncation facilitates purification of the E2 protein without associated E1, and vice versa. The truncated E1 and E2 proteins, when expressed together or combined after expression, are capable of forming a complex.

Accordingly, in one embodiment, the subject invention is directed to an HCV E1 polypeptide, lacking all or a portion of its membrane spanning domain such that the polypeptide is capable of secretion into growth medium when expressed recombinantly in a host cell. In preferred embodiments, the HCV E1 polypeptide lacks at least a portion of its C-terminus beginning at or near about amino acid 370 or about amino acid 360, numbered with reference to the HCV1 E1 amino acid sequence.

In another embodiment, the invention is directed to an HCV E2 polypeptide lacking at least a portion of its membrane spanning domain such that the polypeptide is capable of secretion into growth medium when expressed recombinantly in a host cell, wherein the polypeptide lacks at least a portion of its C-terminus beginning at or near about amino acid 730 but not extending beyond about amino acid 699, numbered with reference to the HCV1 E2 amino acid sequence. In particularly preferred embodiments, the HCV E2 polypeptide lacks at least a portion of its C-terminus beginning at about amino acid 725, numbered with reference to the HCV1 E2 amino acid sequence.

Other embodiments of the subject invention pertain to polynucleotides encoding the above polypeptides, vectors comprising these polynucleotides, host cells transformed with the vectors and methods of recombinantly producing the polypeptides.

In yet another embodiment, the subject invention is directed to a secreted E1/secreted E2 complex comprising:

(a) an HCV E1 polypeptide, lacking all or a portion of its membrane spanning domain such that the E1 polypeptide is capable of secretion into growth medium when expressed recombinantly in a host cell; and (b) an HCV E2 polypeptide, lacking all or a portion of its membrane spanning domain such that said E2 polypeptide is capable of secretion into growth medium when expressed recombinantly in a host cell.

In preferred embodiments, the secreted E1/secreted E2 complex includes an E1 polypeptide which lacks at least a portion of its C-terminus beginning at about amino acid 360 or 370, numbered with reference to the HCV1 E1 amino acid sequence, and said E2 polypeptide lacks at least a portion of its C-terminus beginning at about amino acid 725 or 730, numbered with reference to the HCV1 E2 amino acid sequence.

In still further embodiments, the subject invention is directed to vaccine compositions comprising the truncated HCV E1 and/or E2 polypeptides and/or complexes of the E1 and E2 polypeptides.

These and other embodiments of the present invention will readily occur to those of ordinary skill in the art in view of the disclosure herein.

BRIEF DESCRIPTION OF THE FIGURES

FIG. 1 is a schematic of the E1 region of HCV1.

FIG. 2 shows the nucleotide sequence and corresponding amino acid sequence for HCV1 E1, including the N-terminal signal sequence and the C-terminal membrane anchor domain.

FIGS. 4A–4C show the nucleotide sequence and the corresponding amino acid sequence for the HCV1 E2/NS2 region, including the N-terminal signal sequence for E2 and the C-terminal membrane anchor domain for E2.

DETAILED DESCRIPTION OF THE INVENTION

Figure 3:
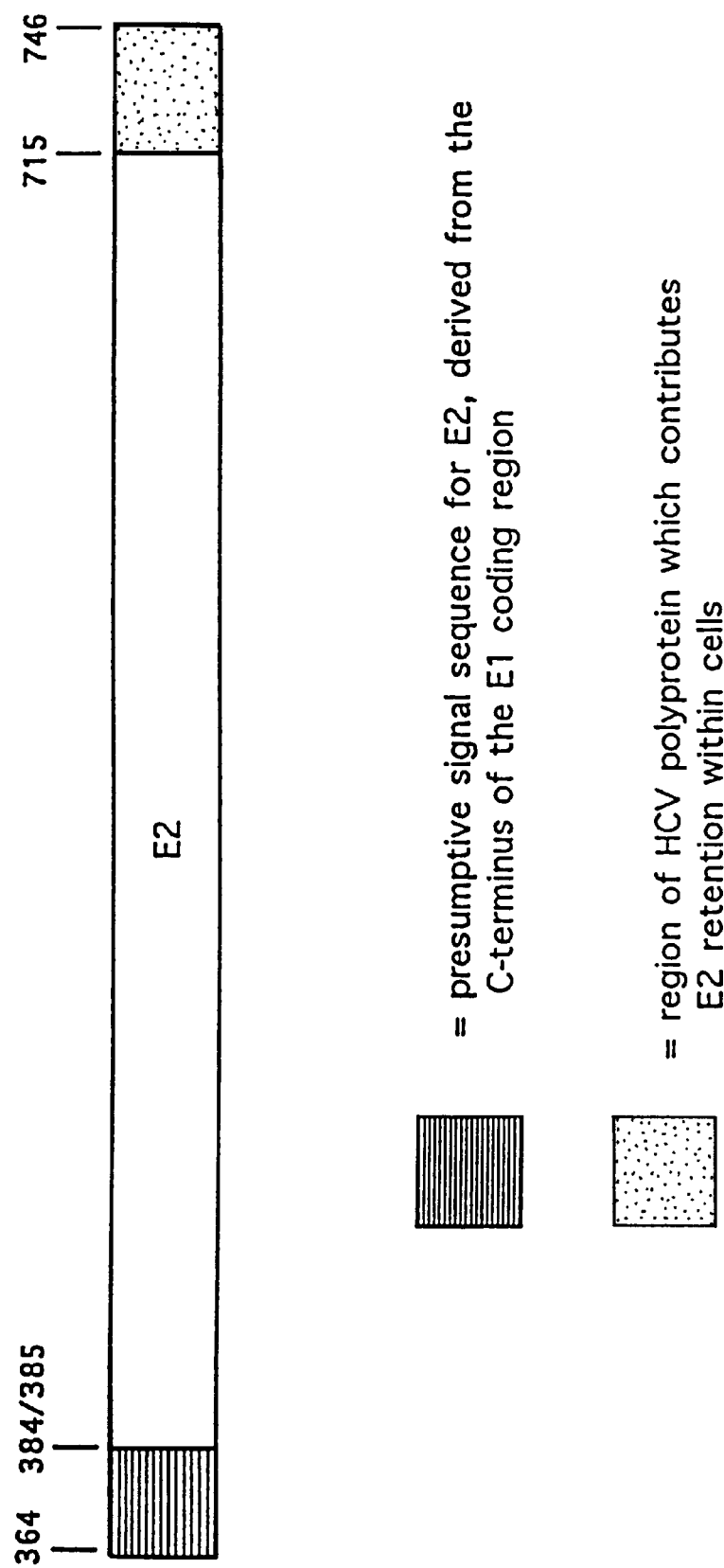
FIG. 3 is a schematic of the E2 region of HCV1.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); *DNA Cloning: A Practical Approach,* vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); *Fundamental Virology,* 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

By an "E1 polypeptide" is meant a molecule derived from an HCV E1 region. Such a molecule can be physically derived from the region or produced recombinantly or synthetically, based on the known sequence. The mature E1 region of HCV1 begins at approximately amino acid 192 of the polyprotein and continues to approximately amino acid 383 (see FIGS. 1 and 2). Amino acids at around 173 through approximately 191 serve as a signal sequence for E1. Thus, by an "E1 polypeptide" is meant either a precursor E1 protein, including the signal sequence, or a mature E1 polypeptide which lacks this sequence, or even an E1 polypeptide with a heterologous signal sequence. Furthermore, as elucidated herein, the E1 polypeptide includes a C-terminal membrane anchor sequence which occurs at approximately amino acid positions 360–383.

By an "E2 polypeptide" is meant a molecule derived from an HCV E2 region. Such a molecule can be physically derived from the region or produced recombinantly or synthetically, based on the known sequence. The mature E2 region of HCV1 is believed to begin at approximately amino acid 384–385 (see FIGS. 3 and 4A–4C). A signal peptide begins at approximately amino acid 364 of the polyprotein. Thus, by an "E2 polypeptide" is meant either a precursor E2 protein, including the signal sequence, or a mature E2 polypeptide which lacks this sequence, or even an E1 polypeptide with a heterologous signal sequence. Furthermore, as elucidated herein, the E2 polypeptide includes a C-terminal membrane anchor sequence which occurs at approximately amino acid positions 715–730 and may extend as far as approximately amino acid residue 746 (see, Lin et al., *J. Virol.* (1994) 68:5063–5073).

Representative E1 and E2 regions from HCV1 are shown in FIGS. 2 and 4A–4C, respectively. For purposes of the present invention, the E1 and E2 regions are defined with respect to the amino acid number of the polyprotein encoded by the genome of HCV1, with the initiator methionine being designated position 1. However, it should be noted that the term an "E1 polypeptide" or an "E2 polypeptide" as used herein is not limited to the HCV1 sequence. In this regard, the corresponding E1 or E2 regions in another HCV isolate can be readily determined by aligning sequences from the two isolates in a manner that brings the sequences into maximum alignment. This can be performed with any of a number of computer software packages, such as ALIGN 1.0, available from the University of Virginia, Department of Biochemistry (Attn: Dr. William R. Pearson). See, Pearson et al., *Proc. Natl. Acad. Sci. USA* (1988) 85:2444–2448.

Furthermore, an "E1 polypeptide" or an "E2 polypeptide" as defined herein is not limited to a polypeptide having the exact sequence depicted in the Figures. Indeed, the HCV genome is in a state of constant flux and contains several variable domains which exhibit relatively high degrees of variability between isolates. As will become evident herein, all that is important is that the region which serves to anchor the polypeptide to the endoplasmic reticulum be identified such that the polypeptide can be modified to remove all or part of this sequence for secretion. It is readily apparent that the terms encompass E1 and E2 polypeptides from any of the various HCV isolates including isolates having any of the 6 genotypes of HCV described in Simmonds et al., *J. Gen. Virol.* (1993) 74:2391–2399). Furthermore, the term encompasses any such E1 or E2 protein regardless of the method of production, including those proteins recombinantly and synthetically produced.

Additionally, the terms "E1 polypeptide" and "E2 polypeptide" encompass proteins which include additional modifications to the native sequence, such as additional internal deletions, additions and substitutions (generally conservative in nature). These modifications may be deliberate, as through site-directed mutagenesis, or may be accidental, such as through naturally occurring mutational events. All of these modifications are encompassed in the present invention so long as the modified E1 and E2 polypeptides function for their intended purpose. Thus, for example, if the E1 and/or E2 polypeptides are to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

An E1 or E2 polypeptide "lacking all or a portion of its membrane spanning domain" is an E1 or E2 polypeptide, respectively, as defined above, which has been C-terminally truncated to delete all or a part of the membrane anchor sequence which functions to associate the polypeptide to the endoplasmic reticulum. Such a polypeptide is therefore capable of secretion into growth medium in which an organism expressing the protein is cultured. The truncated polypeptide need only lack as much of the membrane anchor sequence as necessary in order to effect secretion. Secretion into growth media is readily determined using a number of detection techniques, including, e.g., polyacrylamide gel electrophoresis and the like and immunological techniques such as immunoprecipitation assays as described in the examples. With E1, generally polypeptides terminating with about amino acid position 370 and higher (based on the numbering of HCV1 E1) will be retained by the ER and hence not secreted into growth media. With E2, polypeptides terminating with about amino acid position 731 and higher (also based on the numbering of the HCV1 E2 sequence) will be retained by the ER and not secreted.

It should be noted that these amino acid positions are not absolute and may vary to some degree.

Although not all possible C-terminal truncations have been exemplified herein, it is to be understood that intervening truncations, such as e.g., E1 polypeptides ending in amino acids 351, 352, 353 and so on, or E2 polypeptides ending in for example amino acids 716, 717, 718 and so on, are also encompassed by the present invention. Hence, all E1 polypeptides, terminating at about amino acids 369 and lower, and all E2 polypeptides, terminating at about amino acids 730 and lower, which are capable of secretion into growth medium when expressed recombinantly, are intended to be captured herein.

Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides be secreted and remain functional for their intended purpose. However, particularly preferred E2 constructs will be those with C-terminal truncations that do not extend beyond amino acid position 699.

A "secreted E1/secreted E2 complex" refers to a complex of the E1 and E2 proteins, each of which lacks all or a portion of the membrane spanning domain, as described above. The mode of association of E1 and E2 in such a complex is immaterial. Indeed, such a complex may form spontaneously simply by mixing secreted E1 and E2 proteins which have been produced individually. Similarly, when co-expressed, the secreted E1 and secreted E2 proteins can form a complex spontaneously in the media. Formation of a "secreted E1/secreted E2 complex" is readily determined using standard protein detection techniques such as polyacrylamide gel electrophoresis and immunological techniques such as immunoprecipitation.

Two polynucleotides or protein molecules are "substantially homologous" when at least about 40–50%, preferably at least about 70–80%, and most preferably at least about 85–95%, of the nucleotides or amino acids from the molecules match over a defined length of the molecule. As used herein, substantially homologous also refers to molecules having sequences which show identity to the specified nucleic acid or protein molecule. Nucleic acid molecules that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* vols I & II, supra; *Nucleic Acid Hybridization,* supra.

An "isolated" protein or polypeptide is a protein which is separate and discrete from a whole organism with which the protein is normally associated in nature. Thus, a protein contained in a cell free extract would constitute an "isolated" protein, as would a protein synthetically or recombinantly produced. Likewise, an "isolated" polynucleotide is a nucleic acid molecule separate and discrete from the whole organism with which the sequence is found in nature; or a sequence devoid, in whole or part, of sequences normally associated with it in nature; or a sequence, as it exists in nature, but having heterologous sequences (as defined below) in association therewith.

A "coding sequence" or a sequence which "encodes" a selected protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic DNA sequences. A transcription termination sequence may be located 3' to the coding sequence.

A "polynucleotide" can include, but is not limited to, viral sequences, procaryotic sequences, viral RNA, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

"Control elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control elements need always be present in a recombinant vector so long as the desired gene is capable of being transcribed and translated.

A control element "directs the transcription" of a coding sequence in a cell when RNA polymerase will bind the promoter sequence and transcribe the coding sequence into mRNA, which is then translated into the polypeptide encoded by the coding sequence.

"Operably linked" refers to an arrangement of elements wherein the components so described are configured so as to perform their usual function. Thus, control elements operably linked to a coding sequence are capable of effecting the expression of the coding sequence when RNA polymerase is present. The control elements need not be contiguous with the coding sequence, so long as they functions to direct the expression thereof. Thus, for example, intervening untranslated yet transcribed sequences can be present between, e.g., a promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

A "vector" is a replicon in which a heterologous polynucleotide segment is attached, so as to bring about the replication and/or expression of the attached segment, such as a plasmid, transposon, phage, etc.

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

II. Modes of Carrying Out the Invention

The present invention is based on the discovery of novel E1 and E2 polypeptides which are C-terminally truncated such that they are capable of secretion into growth medium when produced recombinantly in a host cell. The secreted polypeptides are also surprisingly able to form complexes with one another. This interaction is unexpected since, as shown herein, the ability of E1 and E2 to co-precipitate is lost upon elimination of the membrane spanning domain.

In particular, analysis of transient transfections of serially extended templates covering the E2/NS2 region provided evidence for three E2 species with distinct C-termini. One form was E2 terminating at amino acid 729 while the larger two species represented fusions with the downstream NS2A and NS2A/NS2B proteins terminating at amino acids 809 and 1026, respectively. Using the same E2 templates, a region of E2 important for co-immunoprecipitation of E1 has been defined which also prevents E2 secretion. Similarly, a membrane spanning domain of E1 was identified.

More specifically, a membrane spanning domain which presumably serves to anchor E1 to the ER membrane, has been identified at about amino acid positions 360–383. A number of C-terminally truncated E1 polypeptides, lacking portions of this membrane spanning domain, have been constructed. (See FIG. 5). It has been found that E1 polypeptides, ending in amino acid positions 370 and higher, are not secreted into growth media when recombinantly expressed.

Similarly, a series of E2 molecules which include C-terminal truncations as depicted in FIG. 6, have been recombinantly expressed and culture media from transformed cells tested for the presence of the E2 polypeptides to determine which truncated constructs are capable of secretion. It has been found that molecules ending at amino acid positions higher than 730, are not secreted into growth media and presumably are retained in the ER membrane. (It should be noted that a small amount of secretion is observed with constructs terminating at amino acid position 730). An inverse relationship between E2 secretion and its association with E1 has also been found. Hence, the E2 polypeptides which are secretable do not co-precipitate with E1 from lysates whereas those that are not secreted, do.

However, surprisingly, when secreted forms of E1 and E2 polypeptides are co-expressed, the secreted polypeptides are able to form a complex, detectable using antibodies to either of E1 or E2. Such complex formation is significant as it demonstrates that the regions of E1 and E2 which are important for their interaction are retained despite the elimination of C-terminal membrane anchors.

These discoveries provide efficient methods for purifying E1, E2 and secreted E1/E2 complexes, for future use. In particular, secreted proteins are more easily purified than intracellularly expressed proteins. Similarly, since as described above, the native E1 and E2 proteins are known to form a complex, the invention herein described provides a method for obtaining either of E1 or E2 free from the other protein. Additionally, should an E1/E2 complex be desired, the secreted proteins can either be co-expressed or mixed together (either in culture media or in purified or semipurified form), for spontaneous complex formation.

The truncated E1 and E2 polypeptides can be produced using a variety of techniques. For example, the polypeptides can be generated using recombinant techniques, well known in the art. In this regard, oligonucleotide probes can be devised based on the known sequences of the HCV genome and used to probe genomic or cDNA libraries for E1 and E2 genes. The genes can then be further isolated using standard techniques and, e.g., restriction enzymes employed to truncate the gene at desired portions of the full-length sequence. Similarly, the E1 and E2 genes can be isolated directly from cells and tissues containing the same, using known techniques, such as phenol extraction and the sequence further manipulated to produce the desired truncations. See, e.g., Sambrook et al., supra, for a description of techniques used to obtain and isolate DNA. Finally, the genes encoding the truncated E1 and E2 polypeptides can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

Once coding sequences for the desired proteins have been isolated or synthesized, they can be cloned into any suitable vector or replicon for expression. Numerous cloning vectors are known to those of skill in the art, and the selection of an appropriate cloning vector is a matter of choice. Examples of recombinant DNA vectors for cloning and host cells which they can transform include the bacteriophage λ (E. coli), pBR322 (E. coli), pACYC177 (E. coli), pKT230 (gram-negative bacteria), pGV1106 (gram-negative bacteria), pLAFR1 (gram-negative bacteria), pME290 (non-E. coli gram-negative bacteria), pHV14 (E. coli and Bacillus subtilis), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Viral systems, such as a vaccinia based infection/transfection system, as described in Tomei et al., J. Virol. (1993) 67:4017–4026 and Selby et al., J. Gen. Virol. (1993) 74:1103–1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired E1 or E2 polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the E1 or E2 protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as E. coli, Bacillus subtilis, and Streptococcus spp., will find use with the present expression constructs. Yeast hosts useful in the present invention include inter alia, Saccharomyces cerevisiae, Candida albicans, Candida maltosa, Hansenula

*polymorpha, Kluyveromyces fragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda,* and *Trichoplusia ni.*

Depending on the expression system and host selected, the proteins of the present invention are produced by growing host cells transformed by an expression vector described above under conditions whereby the protein of interest is expressed. The protein is then isolated from the host cells and purified. Since the present invention provides for secretion of the E1 and E2 polypeptides, the proteins can be purified directly from the media. The selection of the appropriate growth conditions and recovery methods are within the skill of the art.

The E1 and E2 polypeptides of the present invention can also be produced using conventional methods of protein synthesis, based on the known amino acid sequences. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, New York, (1980), pp. 3–254, for solid phase peptide synthesis techniques; and M. Bodansky, *Principles of Peptide Synthesis,* Springer-Verlag, Berlin (1984) and E.

Gross and J. Meienhofer, Eds., *The Peptides: Analysis, Synthesis,* Biology, supra, Vol. 1, for classical solution synthesis.

As explained above, the present invention also provides a method for producing secreted E1/secreted E2 complexes. Such complexes are readily produced by e.g., co-transfecting host cells with constructs encoding for the E1 and E2 truncated proteins. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the secreted E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured.

The novel, secreted E1 and E2 polypeptides of the present invention, complexes thereof, or the polynucleotides coding therefor, can be used for a number of diagnostic and therapeutic purposes. For example, the proteins and polynucleotides can be used in a variety of assays, to determine the presence of E1 and E2 proteins in a biological sample to aid in the diagnosis of HCV disease. The E1 and E2 polypeptides and polynucleotides encoding the polypeptides can also be used in vaccine compositions, individually or in combination, in e.g., prophylactic (i.e., to prevent infection) or therapeutic (to treat HCV following infection) vaccines. Indeed, such secreted envelope glycoproteins are particularly useful in nucleic acid immunization where secretable molecules may be more effective than the corresponding intracellular proteins in generating an immune response.

The vaccines can comprise mixtures of one or more of the E1 and E2 proteins (or nucleotide sequences encoding the proteins), such as E1 and E2 proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cysl25→ser125), GM-CSF, IL-12, γ-interferon, IP-10, MIP1β and RANTES.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the HCV polypeptide may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; and (6) other substances that act as immunostimulating agents to enhance the effectiveness of the composition. Alum and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy) ethylamine (MTP-PE), etc.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the E1 and/or E2 truncated proteins, or complexes of the proteins, or nucleotide sequences encoding the same, and any other of the above-mentioned components, as needed. By "therapeutically effective amount" is meant an amount of an E1 and/or E2 truncated protein which will induce an immunological response in the individual to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδ T cell populations.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular HCV polypeptide selected and its mode of administration, among other factors. An appropriate effective amount can be readily determined by one of skill in the art. A "therapeutically effective amount" will fall in a relatively broad range that can be determined through routine trials.

Once formulated, the vaccines are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As explained above, vaccines containing polynucletides encoding for the truncated, secreted proteins can be used for nucleic acid immunization. Such a method comprises the introduction of a polynucleotide encoding one or more of the E1 and/or E2 polypeptides into a host cell, for the in vivo expression of the proteins. The polynucleotide can be introduced directly into the recipient subject, such as by injection, inhalation or the like, or can be introduced ex vivo, into cells which have been removed from the host. In the latter case, the transformed cells are reintroduced into the subject where an immune response can be mounted against the protein encoded by the polynucleotide. Methods of nucleic acid immunization are known in the art and disclosed in e.g., International Publication No. WO 93/14778 (published Aug. 5, 1993); International Publication No. WO 90/11092 (published Oct. 4, 1990); Wang et al. *Proc. Natl. Acad. Sci. USA* (1993) 90:4156–4160; Tang et al. *Nature* (1992) 356:152–154; and Ulmer et al. *Science* (1993) 259:1745–1749. Generally, the polynucleotide is administered as a vector which has been encapsulated in a liposome and formulated into a vaccine composition as described above.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Cells and Transient Expression

BSC40 cells and chimpanzee fibroblasts F503 (Perot et al., *J. Gen. Virol.* (1992) 73:3281–3284) were used in infection/transfection experiments as previously described (Selby et al., *J. Gen. Virol.* (1993) 74:1103–1113). Briefly, subconfluent monolayers of cells in 60 mm dishes were infected with $VV_{T7}$ (moi=10) in serum free DME. After 30–60 minutes, the inoculum was removed and replaced with the appropriate cDNA templates cloned into the pTM1 vector (Elroy-Stein and Moss, *Proc. Natl. Acad. Sci. USA* (1990) 87:6743–6747), as described below. Vector DNA was complexed with either Lipofectin (BRL) or Lipofectamine (BRL). After transfection for 2.5–3 hours, the DNA was removed and the cells were starved for 30 minutes in met/cys-deficient DME. Approximately 100–200 $\mu$Ci of $^{35}$S-Express Label (NEN) was added to cells for 3–4 hours. The cells were lysed in 1× lysis buffer (100 mM NaCl, 20 mM Tris-HCL pH 7.5, 1 mM EDTA, 0.5% NP40, 0.5% deoxycholate and 100 mM PMSF, 0.5 ug/ml leupeptin and 2 mg/ml aprotinin), stored on ice for 10 minutes and cleared by centrifugation (15,000×g for 5 minutes). Lysates were immunoprecipitated with the designated antibody immobilized on Protein A Sepharose (BioRad).

HCV Templates

All E1 and E2 templates were generated by PCR and confirmed by sequencing. The appropriate 5' primer containing a methionine residue and an NcoI site was used along with 3' primers that had a termination codon following the designated envelope endpoint and finally, for E1, a BamHI site. Both oligos had non-specific sequences on the ends to facilitate more efficient digestions by NcoI and BamHI enzymes. Digested PCR fragments were ligated into NcoI/BamHI-digested pTM1 (Elroy-Stein and Moss, *Proc. Natl. Acad. Sci. USA* (1990) 87:6743–6747). The pTM1 vector contains the T7 promoter and the EMC leader proximal to the NcoI cloning site which corresponds to the first met residue encoded by the designated DNA. E2 templates were digested with NcoI and AscI and cloned into NcoI (partial)/AscI-pTM1-CE2 (Selby et al., *J. Gen. Virol.* (1993) 74:1103–1113) to generate the H clones where translations began at amino acid 1 and encode core, E1 and the designated E2 regions. For the truncated E1 polypeptides, coding templates began with a methionine residue, followed by isoleucine and then amino acid 172. For the truncated E2 constructs, the methionine at position 364 was used as the N-terminus in the constructions. After identifying possible clones and amplifying the DNA, all were sequenced. All the E1 clones were shown to be correct by sequencing. Most of the E2 clones showed the correct sequence with the exception of the loss of a single leucine residue within E2. This loss did not influence the conclusions as it was not in the vicinity of the C-terminus.

Immunoprecipitations

Immunoprecipitations were performed on media from transfected cells as described in Selby et al., *J. Gen. Virol.* (1993) 74:1103–1113, except that the precipitates were washed at least once with lysis buffer containing 500 mM NaCl instead of 100 mM. The precipitates were resuspended in Laemmli buffer, boiled and analyzed on 12.5% or 15% acrylamide gels. Gels were enhanced (Amplify, Amersham), dried and exposed to film at −80° C. The antisera used were previously described in Selby et al., *J. Gen. Virol.* (1993) 74:1103–1113. Endo H treatments of immunoprecipitates were performed according to the manufacturer's specifications (Oxford Glycosystems).

For the immunoprecipitation of secreted E1 and E2 proteins, media collected from transfected cells was microcentrifuged and immunoprecipitated in tubes containing either monoclonal anti-E1 antibody or rabbit polyclonal anti-E2 antibody immobilized on protein G sepharose (Pharmacia) or protein A sepharose (Sigma), respectively. After an overnight incubation at 4° C., the sepharose Ab-Ag complexes were washed with lysis buffer twice, once with lysis buffer containing 500 mM NaCl and finally with 120 mM Tris, 8.0. After all the liquid was aspirated, approximately 30 μl of Laemmli sample buffer was added, the samples were boiled and then loaded onto a 12.5% acrylamide gel. Following electrophoresis, the gels were fixed, amplified and dried onto 3 MM. The dried gels were exposed to film with an intensifying screen. Transfection controls were done with a template for the β-galactosidase cDNA (pTM1-β-gal).

NS2B Sequencing

BSC40 cells were transfected with pE2$_{1006}$, labeled with $^{35}$S-met (NEN) and lysed with lysis buffer containing protease inhibitors. Cleared lysates were precipitated with rabbit anti-E2 overnight, washed and analyzed on a 15% acrylamide gel. The gel was then transferred to PVDF in 20% methanol/1× running buffer for 2 hours at 50 volts. The region containing NS2B was identified by autoradiography and cut out. NS2B was sequenced via sequential Edmann degradation on a Applied Biosystems 470A gas-phase sequencer (Speicher, (1989). Microsequencng with PVDF membranes: Efficient electroblotting, direct protein adsorption and sequencer program modifications. in *Techniques in Protein Chemistry.* Ed. T. E. Hugli. Academic Press, San Diego, Calif. pp 24–35.). Butyl chloride-containing fractions were evaporated and counted with scintillation fluid.

Example 1

Secretion/Retention of E1

Figure 5:
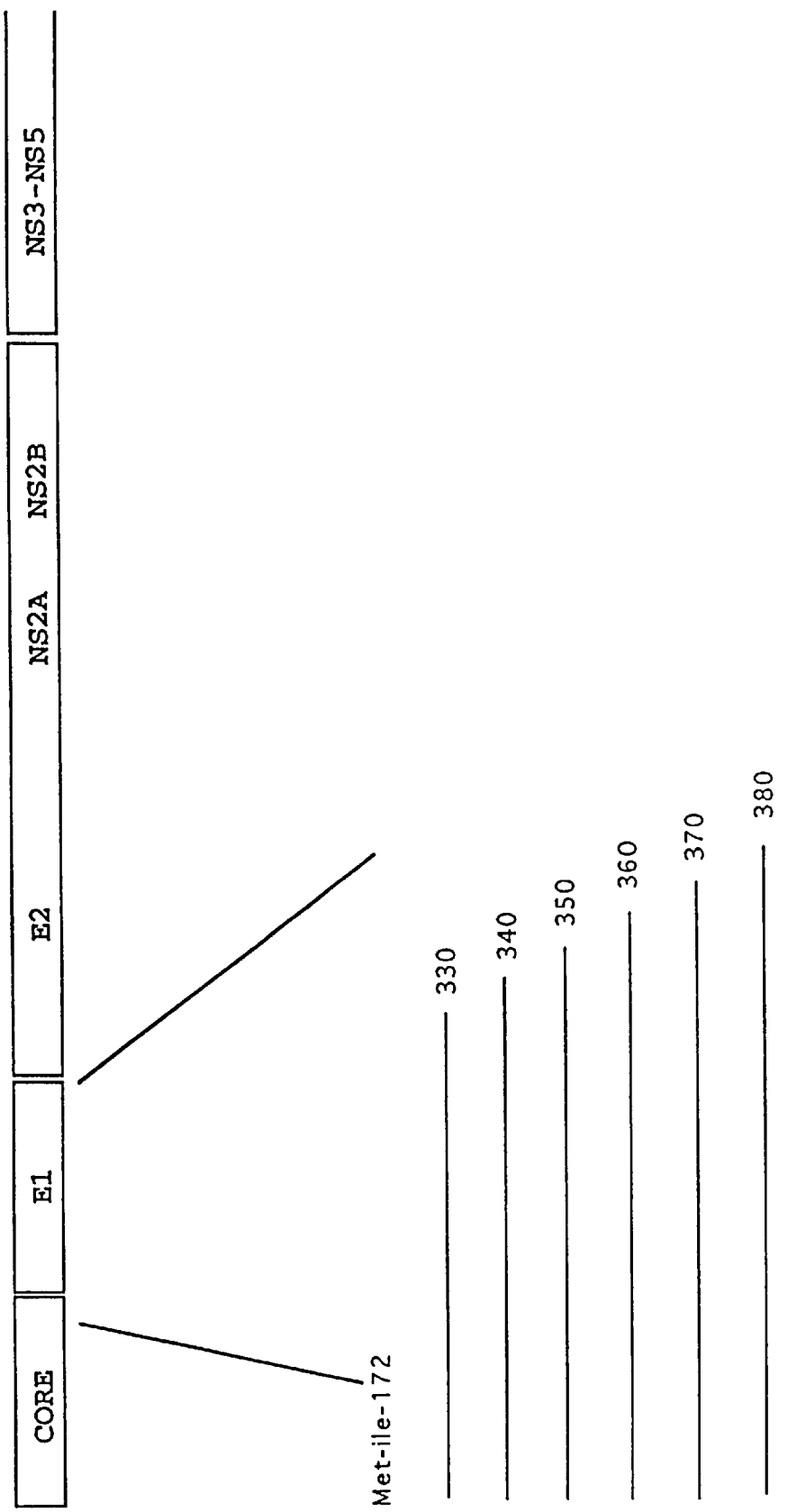
FIG. 5 depicts the HCV E1 cDNA templates used for transfection in the Examples. The core through NS2 region is shown on the top and is drawn to scale; the distal NS3 through NS5 is not drawn to scale. The E1 region has been expanded to better display the templates used. The numbers to the right refer to the amino acid endpoint used in each template.

As explained above, a series of E1 templates were generated in pTM1, using PCR (FIG. 5). In particular, coding templates beginning with a methionine residue, followed by isoleucine and then amino acid 172 of the HCV polyprotein and continuing to amino acid 330, and clones of 10 amino acid increments through amino acid 380, were generated. Amino acids 173 through 191 correspond to the C-terminus of core which apparently serves a role as a signal sequence. Mature E1 is thought to begin at amino acid 192 of the polyprotein following signal sequence cleavage.

Anti-E1 immunoreactive material was recovered in the media of cells transfected with templates through amino acid 360. No E1 was detected in the media of cells transfected with clones terminating at amino acids 370 and 380.

Example 2

Secretion/Retention of E2

Figure 6:
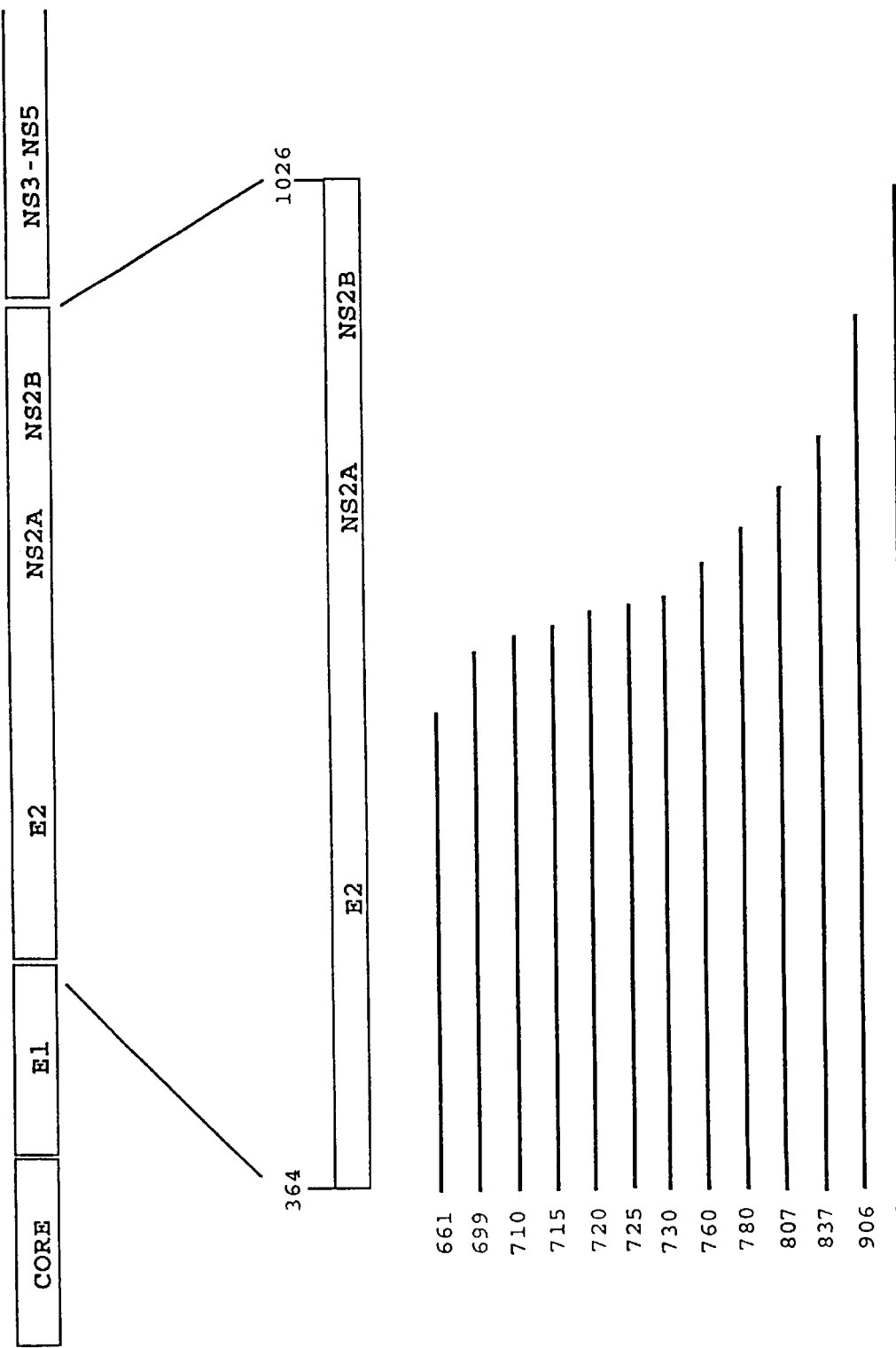
FIG. 6 depicts the HCV E2 cDNA templates used for transfection in the Examples. The core through NS2 region is shown on the top and is drawn to scale; the distal NS3 through NS5 is not drawn to scale. The E2/NS2 region has been expanded to better display the templates used. The column to the left refers to the amino acid endpoint used in each template.

A series of E2 templates were also generated in pTM1, using PCR (FIG. 6). In particular, the first coding amino acid of E2 corresponds to methionine at position 364 and this was used as the N-terminus in the constructions. Amino acid 364 corresponds to the approximate start of the E2 signal peptide (Hijikata et al., *Proc. Natl. Acad. Sci. USA* (1991) 88:5547–5551; Ralston et al., *J. Virol.* (1993) 67:6753–6761). Mature E2 is thought to begin with amino acid 385. The staggered C-termini ranged from amino acid 661 through 1006. In particular, the clones terminated at amino acids 661, 699, 710, 715, 720, 725, 730, 760, 780, 807, 837, 906 and 1006.

Anti-E2 immunoreactive material was recovered in the media of cells transfected with templates through 725. Small amounts of E2 were detected in media transfected with clones terminating at amino acid 730. Little or no E2 was detected in the media of cells transfected with clones terminating at amino acids beyond 730. The sequence just before 730 is quite hydrophobic, reminiscent of a membrane anchor sequence. Thus, it appears that sequences between 715 and 730 and extending as far as approximately amino acid residue 746 (see, Lin et al., *J. Virol.* (1994) 68:5063–5073), serve to anchor E2 to the ER, preventing secretion.

Figure 7:
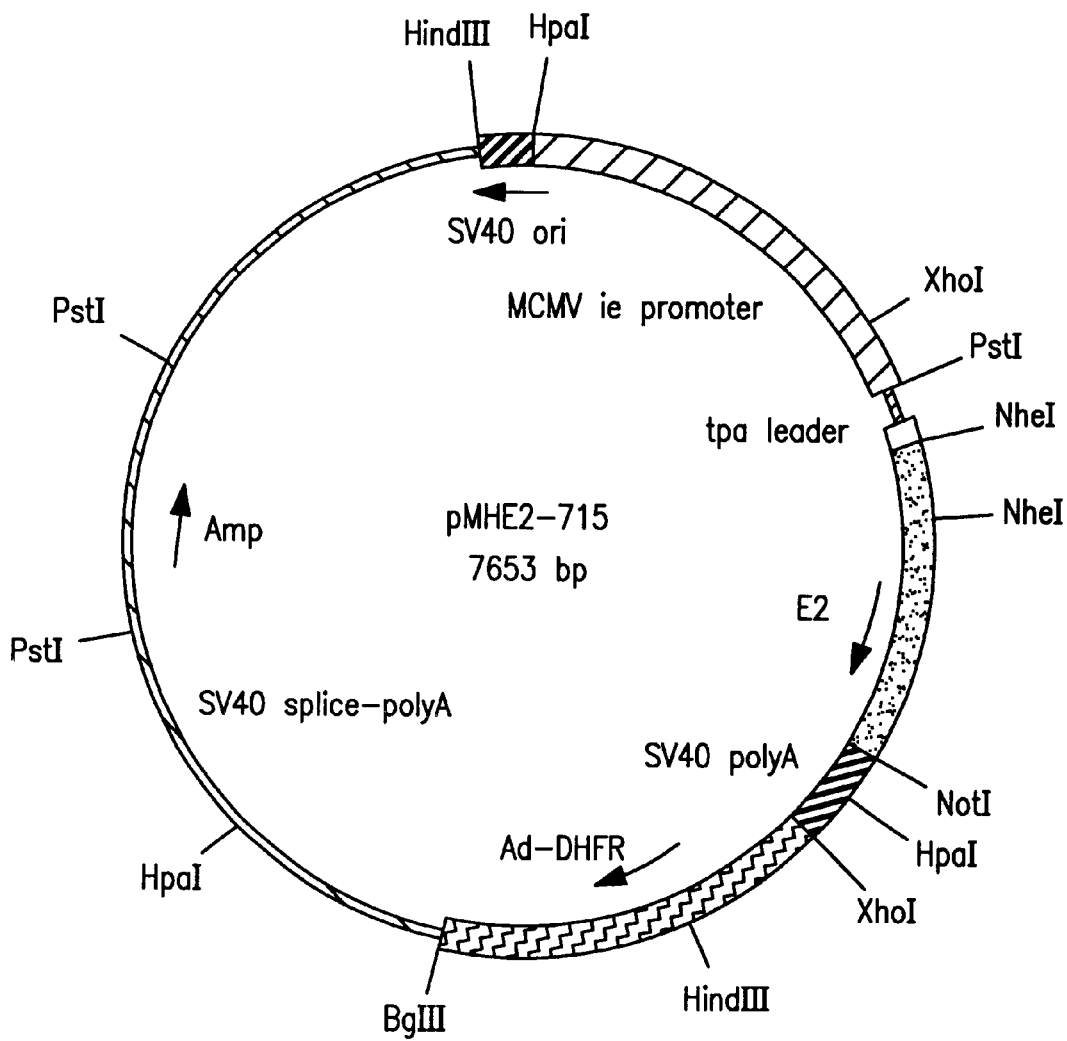
FIG. 7 depicts plasmid pMHE2-715, containing a gene encoding for a truncated E2 protein having amino acids 383–715 of HCV1. Also present in the vector is the SV40 origin of replication, the mouse cytomegalovirus immediate early promoter (MCMV ie), a tpa leader, the SV40 polyadenylation signal and DHFR cDNA for selection.

An additional secreted E2 molecule was made which included amino acids 383$_{ala}$ through 715$_{lys}$. The E2 molecule was expressed using a Chinese hamster ovary cell/dihydrofolate reductase (CHO/DHFR) expression system as follows. A DNA fragment of HCV E2 from amino acid 383 to amino acid 715 of HCV1 was generated by PCR and then ligated into the pMH vector which includes the strong mouse cytomegalovirus immediate early (MCKV ie) promoter and the selectable marker DHFR, to render plasmid pMHE2-715 (see FIG. 7). This plasmid was then stably transfected into the CHO cell line, Dg44, as follows.

100 μg of DNA were combined with lipofectin (Gibco-BRL) for transfection into 1×10$^7$ cells on 10 cm dishes. The cells were transfected and incubated for 24 hours in non-selective medium (Ham's nutrient mixture F-12, JRH Biosciences series no. 51, proline, glutamine and sodium pyruvate) then allowed to recover for 24 hours in non-selective medium supplemented with fetal bovine serum. The non-selective medium was then replaced with selective medium (Ham's nutrient mixture F-12, JRH Biosciences series no. 52, proline, glutamine, and sodium pyruvate) supplemented with dialyzed fetal bovine serum. The medium was changed every 3–4 days until colonies began to form.

The DG44 cell line lacks endogenous DHFR activity. Thus, only those cells transfected with the pMHE2-715 plasmid having the DHFR gene can grow and form colonies in the selective medium which lacks hypoxanthine, aminopterin and thymidine. Approximately 2200 colonies were picked and grown up in 96-well plates. When the clones reached confluency 5 days later, the media was assayed for secreted E2 by ELISA using monoclonal antibody 3E5-1 that was raised against a linear determinant of E2 as the capture antibody and E3 expressed in CHO cells and purified from a monoclonal antibody (5E5H7 reactive to a conformational determinant of E2) affinity column as the standard. The top 83 expressing clones were expanded to 24-well plates. Once confluency was reached in the 24-well plates, the media was assayed and then the top 41 clones were expanded to 6-well plates. When the clones reached confluency, the media was assayed and the top 21 clones were expanded to 75 $cm_2$ flasks. At this point expression was confirmed by the ELISA and by fluorescent immunostaining using the monoclonal antibody 3E5-1. 5 clones had 100% of their cells fluorescing. On the basis of both assays, the top 3 clones were chosen to be purified by limiting dilution.

The top 7 clones were pooled and plated out in 10 cm dishes for growth in a range of methotrexate (MTX) concentrations. MTX is an inhibitor of DHFR. Among a population of cultured cells, variant clones that are overexpressing DHFR are resistant to the toxic MTX. It has been observed that the other genes on a plasmid transfected into CHO cells can be co-amplified with the DHFR gene. The cells expressing HCV E2 were amplified in selective media with final concentrations of 10, 20, 50, 100, 200 nM MTX. Colonies grew up in the 10 and 20 nM MTX media only. These 384 clones were picked, expanded up and checked for expression as done before in the initial selection. In adherent cultures, the top amplified clone had an expression level that was 31% higher than the top unamplified clone and was fluorescing 100%.

Example 3

E2:E1 Co-immunoprecipitation

E1 immunoprecipitates with E2 using monoreactive antisera to E2 or E1 (Grakoui et al., *J. Virol.* (1993) 67:1385–1395; Lanford et al., *Virology* (1993) 197:225–235; Ralston et al., *J. Virol.* (1993) 67:6753–6761). This interaction is very strong as it resists disruption by 0.5% SDS (Grakoui et al., *J. Virol.* (1993) 67:1385–1395) or by high salt/non-ionic detergent (Ralston et al., *J. Virol.* (1993) 67:6753–6761); Glazer and Selby, unpublished observations). To define the region of E2 important for this interaction, BSC40 cells with H templates (core through E2) were transfected and radiolabeled lysates immunoprecipitated with rabbit polyclonal anti-E2 antiserum. E2 species encoded by templates that terminated at amino acid 730, 760 and 780 associated with E1. There was no quantitative difference in E1 co-precipitation with all templates between 730 and 1006. In contrast, E2 species encoded by templates 661, 699, 710, 715, 720 and 725 failed to significantly co-precipitate E1. As a control, the same lysates were immunoprecipitated with patient antiserum LL. E1 proteins from all templates were clearly precipitated with LL; E2 proteins were precipitated efficiently with the exception of template 661H. Relatively poor detection of $E2_{661}$ has consistently been observed, possibly owing to a different structure of this protein compared to longer versions.

Thus, the sequences between amino acids 715 and 730 are important for efficient E1 association. Removal of this C-terminal anchor seems to preclude the association that normally appears between E1 and E2. However, when both envelopes are secreted, it appears that some association occurs. This result is opposite of the secretion data with respect to E2 presented above, thereby establishing an inverse relationship between secretion of E2 and interaction of E2 with E1.

Example 4

Formation of Truncated E1 and E2 Complexes

To test whether truncated forms of E1 and E2, as produced above, were capable of associating with one another, the construct coding for an E1 polypeptide, C-terminally truncated at amino acid 360, was co-transfected with constructs coding for an E2 polypeptide, C-terminally truncated at amino acid 715 or an E2 polypeptide, C-terminally truncated at amino acid 725. Cells were transformed as described above and media collected. E1/E2 complexes were observed clearly with anti-E2 monoclonal antibody where E1 was co-precipitated. The converse precipitation with monoclonal anti-E1 yielded much less E1 compared to the former precipitation. A similar observation was made in Ralston et al., *J. Virol.* (1993) 67:6753–6761, with respect to non-truncated constructs. Such complex formation is significant because it demonstrates that the regions of E1 and E2 important for their interaction are retained, despite elimination of all or a part of the membrane spanning domains.

Example 5

Multiple E2 Species: Endo H Studies

Three E2 bands resulted from endo F treatment of E2, suggesting that more than one E2 species exists although the endpoints remain undefined (Grakoui et al., *J. Virol.* (1993) 67:1385–1395). Furthermore, a high molecular weight band reactive with both E2 and NS2 antisera led to the speculation of a possible E2-NS2 species (Grakoui et al., *J. Virol.* (1993) 67:1385–1395; Tomei et al., *J. Virol.* (1993) 67:4017–4026). Endo H treatment was used to define these three E2 glycoproteins. Endo H is a suitable deglycosidase for these experiments as only immature, high mannose glycoproteins are observed in transient expression systems (Spaete et. al., *Virology* (1992) 188:819–830; Ralston et al., *J. Virol.* (1993) 67:6753–6761). Endo H treatment of E2 proteins encoded by templates $E2_{661}$ through $E2_{730}$ yielded single bands that increased in size concomitantly with the elongated templates. Endo H-treated E2 proteins encoded by templates $E2_{760}$, $E2_{780}$ and $E2_{807}$ showed an additional band that stopped increasing in size at amino acid 807 when compared to longer templates. These data suggest that one form of E2 terminates near amino acid 730. Recent data suggest that E2 may terminate at about amino acid 746 (see, Lin et al., *J. Virol.* (1994) 68:5063–5073). A second form of E2 appears to terminate near amino acid position 807. On templates $E2_{906}$ and $E2_{1006}$ a third band was note which migrated higher than the previous doublet. The sizes of the bands from these two templates were consistent with E2 molecules that were encoded by the entire templates. The mobility of E2-NS2 fusion in pTM1-HCV was slightly decreased relative to $E2_{1006}$. These observations are consistent with the third form of E2 ending co-incidentally with the NS2/NS3 junction at amino acid 1026 (Grakoui et al., *Proc. Natl. Acad. Sci. USA* (1993) 90:10583–10587).

NS2 has been identified preceding NS3 (Grakoui et al., *J. Virol.* (1993) 67:1385–1395; Hijikata et al., *Proc. Natl. Acad. Sci. USA* (1993) 90:10773–10777; Selby et al., *J. Gen. Virol.* (1993) 74:1103–1113). The results presented here and other recent reports (Lin et al., *J. Virol.* (1994) 68:5063–5073) support differential precursor processing whereby extensions of E2 beyond amino acids 730–746 represent E2 fusions to NS2. We tentatively suggest that the small protein coding region approximately between amino acids 730–746 and 807 predicted by the endo H experiments corresponds to NS2A while the downstream protein is NS2B. This nomenclature is based on the similar organization of proteins amongst the Flaviviridae. It is possible that NS2A is not independently cleaved from the polyprotein as is NS2B and it remains to be determined if NS2A is in fact a non-structural protein.

Example 6

NS2B: E2: Co-immunoprecipitation and the N-terminus of NS2B

Patient serum LL detected the E2 glycoproteins and two other species of 14 kDa and 21 kDa from transfections with templates $E2_{906}$ and $E2_{1006}$. These latter species correspond to NS2B because the difference in size correlates perfectly with the difference in the template lengths and a 23 kDa NS2B was detected from the full-length HCV template, pTM1-HCV (Selby et al., *J. Gen. Virol.* (1993) 74:1103–1113). When an anti-E2 antibody was used to immunoprecipitate the same lysates, NS2B co-precipitated with E2. Under these conditions E1 also co-immunoprecipitates. Additionally, higher anti-E2 reactive species were also seen in 906, 1006 and pTM1-HCV precipitations, which correspond to E2 fusions with NS2A and different lengths of NS2B.

Using the various E2 templates, we defined one region of E2 important for co-precipitation of NS2B. E2 templates ending at amino acids 699, 730, 760, 780 and 807 were co-transfected with pTM1-NS25, which encodes amino acids 730 through 3011 (Selby et al., *J. Gen. Virol.* (1993) 74:1103–1113). pTM1-NS25 was used since this template was previously determined to encode NS2 and an independent template was required for NS2B expression to define sequences important for the E2:NS2B interaction. Anti-E2 antibody immunoprecipitated E2 proteins and also co-precipitated NS2B (23 kDa) and probable NS4B (27 kDa) from all lysates except from that transfected with the $E2_{699}$ template. As a positive control, truncated NS2B from the $E2_{1006}$ template was co-precipitated with E2. These data demonstrate that amino acids 699 through 730 are important for NS2B and NS4B association with E2.

The anti-E2 antibody that co-precipitated NS2B was made against an SOD-E2 fusion that terminated at amino acid 662. This excludes the possibility of cross-reactivity to NS2B as a cause for NS2B detection. This NS2B band was not glycosylated as evidenced by its insensitivity to endo H treatment. Because co-precipitation of NS2B was with little background and efficient, this association property was used to radio-sequence the N-terminus of NS2B. The immunoprecipitate of the $^{35}$S-methionine-labeled lysate from an $E2_{1006}$ transfection was analyzed on a 15% acrylamide gel and transferred to PVDF for sequencing. Using a methionine residue 18 amino acids away from residue 810 as a reference, the amino terminus of NS2B was identified as amino acid 810. This assignment agrees with the predicted E2 C-terminus based on the endo H pattern from the E2 deletion templates and confirms the cleavage sites recently reported by Grakoui et al., *Proc. Natl. Acad. Sci. USA* (1993) 90:10583–10587 and Mizushima et al., *J. Virol.* (1994) 68:2731–27341994. The presumptive NS2A termini is predicted to reside as amino acids 730 and 809 if its exists as an independent protein.

Thus, novel secreted E1 and E2 forms are disclosed. Although preferred embodiments of the subject invention have been described in some detail, it is understood that obvious variations can be made without departing from the spirit and the scope of the invention as defined by the appended claims.

What is claimed is:

1. A method of producing a secreted HCV polypeptide, said method comprising:
   (a) providing a population of mammalian or yeast host cells;
   (b) transforming said host cells with a recombinant vector comprising (i) a polynucleotide encoding an HCV E2 polypeptide having a C-terminus at about amino acid residue 715, numbered with reference to the HCV1 E2 amino acid sequence and (ii) control elements that are operably linked to said coding sequence whereby said coding sequence can be transcribed and translated in the host cell, and
   (c) culturing said host cells under conditions whereby said HCV polypeptide is expressed and secreted.

2. The method of claim 1, wherein the N-terminus of said polypeptide is about amino acid 383, numbered with reference to the HCV1 E2 amino acid sequence.

3. The HCV polypeptide produced according to the method of claim 1.

4. The HCV polypeptide produced according to the method of claim 2.

* * * * *